(12) United States Patent
Aleo et al.

(10) Patent No.: US 8,680,078 B2
(45) Date of Patent: Mar. 25, 2014

(54) STABLE OPHTHALMIC FORMULATIONS

(75) Inventors: Danilo Aleo, Scicli (IT); Sergio Mangiafico, Solarino (IT); Maria Grazia Antonietta Saita, Niscemi (IT)

(73) Assignee: Medivis SRL (IT)

( * ) Notice: Subject to any disclaimer, the term of this patent is extended or adjusted under 35 U.S.C. 154(b) by 481 days.

(21) Appl. No.: 12/936,640

(22) PCT Filed: Nov. 7, 2008

(86) PCT No.: PCT/IB2008/003381
§ 371 (c)(1),
(2), (4) Date: Oct. 6, 2010

(87) PCT Pub. No.: WO2009/125246
PCT Pub. Date: Oct. 15, 2009

(65) Prior Publication Data
US 2011/0028477 A1 Feb. 3, 2011

Related U.S. Application Data

(60) Provisional application No. 61/110,395, filed on Oct. 31, 2008.

(30) Foreign Application Priority Data

Apr. 7, 2008 (IT) .............................. RM2008A0182

(51) Int. Cl.
*A61K 31/67* (2006.01)
*A61K 31/215* (2006.01)

(52) U.S. Cl.
USPC .............................. 514/96; 514/530; 514/912

(58) Field of Classification Search
USPC ........................................... 514/96, 530, 912
See application file for complete search history.

(56) References Cited

U.S. PATENT DOCUMENTS 6,313,155 B1 11/2001 Sponsel

FOREIGN PATENT DOCUMENTS

| EP | 1759702 | 3/2007 |
| WO | WO-9415582 | 7/1994 |
| WO | WO-02-38158 A1 | 5/2002 |
| WO | WO-2006-082588 A2 | 8/2006 |
| WO | WO-2009-125246 A1 | 10/2009 |

OTHER PUBLICATIONS

EP8873876 Response to Communication filed Apr. 25, 2012.
EP8873876 Communication Report mailed Dec. 15, 2011.
PCT/IB2008/003381 IPRP mailed Oct. 12, 2010.
PCT/IB08/00338 Search Report and Written Opinion mailed Oct. 15, 2009.
Sigurdsson et al. Cyclodextrin formulation of dorzolamide and its distribution in the eye after topical administration. J Control Release. Jan. 20, 2005;102(1):255-262.
Loftsson, T., et al., "Topical drug delivery to the eye: dorzolamide," Acta Ophthalmologica, vol. 90, pp. 603-608, (2012).
Akorn, Inc., Package Insert for Latanoprost Solution, pp. 1-5.
American Reagent, Inc., Package Insert for Latanoprost Solution, pp. 1-6.
Apotex Corp., Package Insert for Latanoprost Solution, pp. 1-5.
Bausch & Lomb Incorporated, Package Insert for Latanoprost Solution, pp. 1-6.
Falcon Pharmaceuticals, Ltd., Package Insert for Latanoprost Solution, pp. 1-5.
Greenstone, LLC, Package Insert for Latanoprost Solution, pp. 1-5.
Mylan Pharmaceuticals, Inc., Package Insert for Latanoprost Solution, pp. 1-6.
Quint, M.P., et al., "Dorsolamide Hydrochloride" Analytical Profiles of Drug Profiles and Excipients, vol. 26, pp. 284-317, 1999.
Rebel Distributors Corp., Package Insert for Latanoprost Solution, pp. 1-5.
Xalatan®, Package Insert for Latanoprost Solution, pp. 1-7.

*Primary Examiner* — Zohreh Fay
(74) *Attorney, Agent, or Firm* — Wilson, Sonsini, Goodrich & Rosati

(57) ABSTRACT

Disclosed herein are stable formulations suitable for the treatment of glaucoma and ocular hypertension.

17 Claims, No Drawings

US 8,680,078 B2

STABLE OPHTHALMIC FORMULATIONS

RELATED APPLICATIONS

This application is a 35 U.S.C. 371 (national stage) application of PCT/IB2008/003381 filed Nov. 7, 2008, which claims the benefit of Italian Patent Application No. RM2008A000182 filed Apr. 7, 2008, and the benefit of U.S. Provisional Patent Application No. 61/110,395 filed Oct. 31, 2008, all of which are herein incorporated by reference in their entirety.

FIELD OF THE APPLICATION

Described herein are composition and methods for treating ophthalmic conditions.

BACKGROUND OF THE INVENTION

Glaucoma is an ophthalmic disease that often manifests as a progressive increase in intraocular pressure. Untreated glaucoma leads to severe defects in the structure of the eye, particularly to damage of the head of the optic nerve, resulting in reduction of the visual field and optical atrophy. In certain instances, the pathology is related to insufficient drainage of aqueous humor from the eye. Other factors, including the production of aqueous humor and pressure on the episcleral veins, may also contribute to development of the condition.

SUMMARY OF THE INVENTION

Provided herein are stable ophthalmic formulations for the treatment of ophthalmic conditions, including conditions in which intraocular pressure (IOP) is greater than 21 mm Hg ("high IOP"). Such compositions include, by way of example only, gel, ointments, solutions, viscous solutions, eye drops, emulsions, gel-forming solutions and the like. In some embodiments, the compositions are not in the form of suspensions. The stable ophthalmic formulations are used for the treatment of glaucoma, ocular hypertension, or combinations thereof. Further, the stable ophthalmic formulations described herein are used for treating high IOP resulting from traumatic hyphema, orbital edema, postoperative visco-elastic retention, intraocular inflammation, corticosteroid use, pupillary block, or idiopathic causes. In some embodiments, the stable ophthalmic formulations have at least one stability selected from chemical stability, physical stability and physiological stability. In further embodiments, the stable ophthalmic formulations have at least two of the aforementioned types of stability. In yet further embodiments, the stable ophthalmic formulations possess all three of the aforementioned types of stability.

In certain embodiments, the stable ophthalmic formulations have a pH between about 5.8 and 6.5, including a pH selected of about 5.8, about 5.9, about 6.0, about 6.1, about 6.2, about 6.3, about 6.4 or about 6.5, and further, solubilized dorzolamide (or a pharmaceutically acceptable salt thereof), including by way of example, dorzolamide complexed with a type of cyclodextrin. In one embodiment, the formulations are stable during storage at temperatures of about 20° C. and above (including at temperatures of about 25° C. and above; at temperatures of about 28° C. and above; at temperatures of about 30° C. and above) for extended periods of time, and are well-tolerated when administered to the eye, even during long-term therapy. In certain embodiments, the cyclodextrin is hydroxypropyl-β-cyclodextrin (HP-β-cyclodextrin). Such stable ophthalmic formulations include, by way of example only, gel, ointments, solutions, viscous solutions, eye drops, emulsions, gel-forming solutions and the like. In some embodiments, the stable ophthalmic formulations are not in the form of suspensions.

In certain embodiments, the stable ophthalmic formulations comprise a combination of dorzolamide or a pharmaceutically acceptable salt thereof and latanoprost at therapeutically effective concentrations. In one embodiment, the formulations are stable (i.e., chemically, physically and physiologically stable) during storage at temperatures 20° C. and above (including at temperatures of about 25° C. and above; at temperatures of about 28° C. and above; at temperatures of about 30° C. and above) for extended periods of time, and are well-tolerated when administered to the eye, even during long-term therapy. The formulations disclosed herein comprise a stabilizing and solubilizing system that simplifies coadministration of the active agents. The stabilizing and solubilizing system comprises a cyclodextrin and a pH in a range that maintains the integrity of the active agents and is well-tolerated by the eye. In certain embodiments, the cyclodextrin is hydroxypropyl-β-cyclodextrin (HP-β-cyclodextrin). In some embodiments, the pH is between about 5.8 and 6.5, including a pH selected of about 5.8, about 5.9, about 6.0, about 6.1, about 6.2, about 6.3, about 6.4 or about 6.5. Such stable ophthalmic formulations include, by way of example only, gel, ointments, solutions, viscous solutions, eye drops, emulsions, gel-forming solutions and the like. In some embodiments, the stable ophthalmic formulations are not in the form of suspensions.

In some embodiments, a stable ophthalmic composition disclosed herein for the treatment of high IOP, including glaucoma, ocular hypertension, or a combination thereof comprises a cyclodextrin and a therapeutically effective amount of a therapeutic component, wherein the composition has a pH that is well-tolerated by the eye and maintains stability of the therapeutic component, and wherein the therapeutic component comprises dorzolamide or a pharmaceutically acceptable salt thereof and latanoprost. In one embodiment, the formulations are stable during storage at temperatures 20° C. and above (including at temperatures of about 25° C. and above; at temperatures of about 28° C. and above; at temperatures of about 30° C. and above) for extended periods of time, and are well-tolerated when administered to the eye, even during long-term therapy. In some embodiments, after 6 months of storage at 25° C., a stable ophthalmic composition disclosed herein comprises at least 97% of the initial amount of dorzolamide, and at least 98% of the initial amount of latanoprost. In some embodiments, after 6 months of storage at 40° C., a stable ophthalmic composition disclosed herein comprises at least 97% of the initial amount of dorzolamide, and at least 98% of the initial amount of latanoprost. Such stable ophthalmic composition include, by way of example only, gel, ointments, solutions, viscous solutions, eye drops, emulsions, gel-forming solutions and the like. In some embodiments, the stable ophthalmic compositions are not in the form of suspensions.

In certain embodiments, an ophthalmic composition disclosed herein for the treatment of high IOP, including glaucoma, ocular hypertension, or a combination thereof comprises a cyclodextrin and a therapeutically effective amount of a therapeutic component, wherein the composition has a pH between 5.8 and 6.5, and wherein the therapeutic component comprises dorzolamide or a pharmaceutically acceptable salt thereof and latanoprost. In some embodiments, the pH is between about 5.8 and 6.5, including a pH selected of about 5.8, about 5.9, about 6.0, about 6.1, about 6.2, about 6.3, about 6.4 or about 6.5. In some embodiments, the pharmaceutically acceptable salt of dorzolamide is dorzolamide hydrochloride. In certain embodiments, the cyclodextrin is HP-β-cyclodextrin. In some specific embodiments, a composition disclosed herein comprises dorzolamide hydrochloride at 0.025-5 wt %, latanoprost at 0.001-5 wt %, and HP-β-cyclodextrin at 0.01-50 wt %. In certain embodiments, a composition disclosed herein comprises dorzolamide hydrochloride at 1-3 wt %, latanoprost at 0.003-0.01 wt %, and HP-β-cyclodextrin at 2-10 wt %.

In some embodiments, a composition disclosed herein further comprises at least one agent selected from a mucoadhesive, a preservative, a pH-adjusting agent, a tonicity-adjusting agent, a buffering agent, an antioxidant, a chelating agent, an antimicrobial preservative, a chemical preservative, or a combination thereof. In some embodiments, the mucoadhesive is hyaluronic acid or a pharmaceutically acceptable salt thereof (e.g., sodium hyaluronate), polyvinyl alcohol, polyvinyl-pyrrolidone, hydroxypropyl methylcellulose, carboxymethyl cellulose, hydroxyethyl cellulose, a poloxamer, alginic acid, chitosan, xanthan gum, carrageenan, acrylic acid, acrylic acid derivatives, or a combination thereof. In some embodiments, the preservative is benzalkonium chloride, chlorobutanol, phenylmercuric acetate, phenylmercuric nitrate, polyhexanide, cetrimide, cetylpyridinium chloride, EDTA, or a combination thereof. In some embodiments, the pH-adjusting agent is hydrochloric acid, boric acid, acetic acid, sodium hydroxide, potassium hydroxide, or a combination thereof. In some embodiments, the tonicity-adjusting agent is sodium chloride, potassium chloride, mannitol, glycerol, sorbitol, xylitol, or a combination thereof. In some embodiments, the buffering agent is boric acid, an acetate buffer, a citrate buffer, a phosphate buffer, a borate buffer, or a combination thereof. In some embodiments, the antioxidant is sodium metabisulfite, sodium thiosulfate, acetyl cysteine, BHA, BHT, vitamin E, ascorbic acid, 6-hydroxy-2,5,7,8-tetramethylchroman-2-carboxylic acid, or a combination thereof. Such composition include, by way of example only, gel, ointments, solutions, viscous solutions, eye drops, emulsions, gel-forming solutions and the like. In some embodiments, the compositions are not in the form of suspensions.

In some embodiments, a composition or formulation disclosed herein does not contain a buffer system. In further embodiments, a composition or formulation disclosed herein does not contain an antioxidant. In some embodiments, a composition disclosed herein contains neither a buffer system nor an antioxidant. In some embodiments, a composition or formulation disclosed herein does not contain a antimicrobial preservative.

In some embodiments, a composition disclosed herein further comprises a therapeutically effective amount of an additional anti-glaucoma agent. In certain embodiments, the additional anti-glaucoma agent is a beta blocker. In certain specific embodiments, the beta blocker is timolol.

Further disclosed herein is a method of treating high IOP, including glaucoma, ocular hypertension, or a combination thereof comprising topically administering a composition disclosed herein to the eye of a patient in need thereof.

Also disclosed herein is a method of stabilizing an ophthalmic composition comprising dorzolamide or a pharmaceutically acceptable salt thereof and latanoprost, said method comprising incorporating a cyclodextrin into the formulation and adjusting the pH to a range that is well-tolerated by the eye and maintains stability of each of the active agents. In some embodiments, after 6 months of storage at 25° C., the composition stabilized by the method comprises at least 97% of the initial amount of dorzolamide, and at least 98% of the initial amount of latanoprost. In some embodiments, after 6 months of storage at 40° C., the composition stabilized by the method comprises at least 97% of the initial amount of dorzolamide, and at least 98% of the initial amount of latanoprost. In some embodiments, the cyclodextrin used in the method of stabilizing a composition comprising dorzolamide or a pharmaceutically acceptable salt thereof and latanoprost is HP-β-cyclodextrin.

DETAILED DESCRIPTION OF THE INVENTION

Provided herein are compositions comprising at least two different active agents. In other words, provided herein are compositions comprising a first active agent and a second active agent. In specific embodiments, the first active agent is a carbonic anhydrase inhibitor (e.g., dorzolamide or a pharmaceutically acceptable salt thereof, such as dorzolamide hydrochloride). In specific embodiments, the second active agent is a hypotensive agent (e.g., an ophthalmic hypotensive agent). In more specific embodiments, the hypotensive agent is a prostaglandin (e.g., a $PGF_{2\alpha}$ prostaglandin such as latanoprost). In further embodiments, compositions described herein optionally comprise one or more additional active agents (e.g., a third active agent, a fourth active agent, and the like). In some embodiments, the compositions described herein are pharmaceutical compositions. In certain embodiments, the pharmaceutical compositions described herein are formulated for topical administration. In further or alternative embodiments, the compositions described herein are formulated for ophthalmic administration (e.g., as a collyrium). In certain embodiments, ophthalmic compositions and formulations described herein are well-tolerated by the eye. In some embodiments, ophthalmic formulations described herein are useful for the treatment of high IOP, including glaucoma, ocular hypertension, or a combination thereof. Such ophthalmic formulations include, by way of example only, gel, ointments, solutions, viscous solutions, eye drops, emulsions, gel-forming solutions and the like. In some embodiments, the ophthalmic formulations are not in the form of suspensions.

In certain instances, compositions and formulations described herein comprise a first active agent suitable for the treatment of high IOP including glaucoma, ocular hypertension, or a combination thereof and a second active agent suitable for the treatment of high IOP including glaucoma, ocular hypertension, or a combination thereof. In certain instances, compositions and formulations described here simplify coadministration of the at least two different active agents for the treatment of high IOP including glaucoma, ocular hypertension, or a combination thereof. In some instances, coadministration of the at least two different active agents in a single formulation results in an additive or synergistic treatment efficacy relative to administration of the agents individually and/or separately. In some instances, coadministration of the active agents in a single formulation reduces the possibility of dosing errors or missed treatments that result from administration of the compounds in separate formulations. Thus, in certain instances, coadministration of the active agents in a formulation disclosed herein results in overall better patient compliance for the treatment of high IOP including glaucoma, ocular hypertension, or a combination thereof with the at least two different actives.

In certain embodiments, a composition or formulation described herein comprises a first active agent and/or the second active agent, both of which are solubilized in a liquid medium (aqueous medium). In some embodiments, at least one of the solubilized active agents is complexed with a complexing agent and the combination thereof is dissolved.

In some embodiments, the active agent is dissolved without being complexed by a complexing agent. In some embodiments, the complexing agent is a cyclodextrin. In some embodiments, at least one active agent forms an inclusion complex with the cyclodextrin.

In some embodiments, compositions and formulations described herein comprise a first active agent and a second active agent, wherein the first active agent and the second active agent are formulated into the composition or formulation in a manner that allows ophthalmic and/or topical activity of the agents (e.g., by formulating a composition or formulation described herein as a solution, gel, or the like, comprising a first active agent and a second active agent as solutes within the solution, gel, etc.). It is to be understood that such compositions and formulations include compositions and formulations wherein a substantial portion, a therapeutically effective portion, most or all of the first and second agents are dissolved in the liquid medium (e.g., aqueous medium).

In some embodiments, compositions and formulations described herein comprise a stabilizing agent. In certain embodiments, the stabilizing agent enhances the chemical stability (e.g., inhibition of degradation of one or more of the active agents present), physiological stability (i.e., post-administration degradation) and/or physical stability (e.g., substantially maintaining the concentration of one or more of the active agents dissolved in the liquid medium) of the composition or formulation. In specific embodiments, stabilizing agents useful herein include, by way of non-limiting example, one or more cyclodextrin (e.g., hydroxypropyl-β-cyclodextrin).

In specific embodiments, provided herein are stable compositions and formulations comprising a carbonic anhydrase inhibitor (e.g., dorzolamide or a pharmaceutically acceptable salt thereof, such as dorzolamide hydrochloride), and a hypotensive agent (e.g., a prostaglandin, including, by way of non-limiting example, a $PGF_{2\alpha}$ prostaglandin such as latanoprost). In more specific embodiments, provided herein are stable compositions and formulations comprising a carbonic anhydrase inhibitor (e.g., dorzolamide or a pharmaceutically acceptable salt thereof, such as dorzolamide hydrochloride), a hypotensive agent (e.g., a prostaglandin, including, by way of non-limiting example, a $PGF_{2\alpha}$ prostaglandin such as latanoprost), and an aqueous medium. In still more specific embodiments, provided herein are stable compositions and formulations comprising a carbonic anhydrase inhibitor (e.g., dorzolamide or a pharmaceutically acceptable salt thereof, such as dorzolamide hydrochloride), a hypotensive agent (e.g., a prostaglandin, including, by way of non-limiting example, a $PGF_{2\alpha}$ prostaglandin such as latanoprost), an aqueous medium, and a stabilizing agent (e.g., a cyclodextrin, such as hydroxypropyl-β-cyclodextrin). In certain embodiments, such compositions are well-tolerated by the eye.

In some embodiments, any of the compositions or formulations described herein are stable compositions or formulations. Included within the concept of stable compositions or formulations are the chemical stability, physiological, and/or physical stability of the composition or formulation. In some embodiments, the stability is provided by use of a stabilizer and/or by adjusting the pH to between about 5.8 and about 6.5. In some embodiments, the stabilizer is a cyclodextrin. In some embodiments, the stabilizer provides one form of stability to one active ingredient (e.g., physical stability) and another form of stability to a second active ingredient (e.g., chemical stability).

In certain instances, chemical stability refers to the inhibition of degradation of one or more of the active agents present. In some embodiments, chemical stability of a composition or formulation described herein includes the chemical stability of at least one active agent, the first active agent, the second active agent, or all active agents present in the composition or formulation. In certain instances, chemical stability refers to the stability of a composition, formulation, or agent against degradation. Thus, in some instances, the chemical stability of an agent is determined by measuring the amount of the agent that is present at an initial time (e.g., at the time of formulation) and a second later time; and determining the amount or percent decrease in the agent over the time between the initial time and the second later time.

In some instances, physical stability refers to substantially maintaining constitution of the formulation or composition. In certain embodiments wherein a composition or formulation described herein comprises at least two different active agents and a liquid medium (e.g., an aqueous medium), physical stability refers to the maintenance of a substantially similar amount and/or therapeutically effective amount of the active agents dissolved in the liquid medium. Thus, in certain instances, agents that enhance the physical stability of a composition or formulation described herein include solubilizers.

In some instance, physiological stability refers to substantially maintaining the therapeutic activity of the dorzolamide and/or latanoprost after administration of the ophthalmic formulation to the eye. That is, stabilization to physiological degradation of the active agents.

In some embodiments, the stable compositions or formulations are formulated with a pH between about 5.8 and 6.5, including a pH selected of about 5.8, about 5.9, about 6.0, about 6.1, about 6.2, about 6.3, about 6.4 or about 6.5. In certain embodiments, stability includes chemical, physiological, and/or physical stability. In certain embodiments, the compositions or formulations are stable during storage at temperatures 20° C. and above for extended periods of time, and are well-tolerated when administered to the eye, even during long-term therapy.

In certain embodiments, provided herein are methods of treating glaucoma in an individual comprising administering to an individual in need thereof an effective amount of any composition or formulation described herein. In some embodiments, provided herein are methods of treating ocular hypertension in an individual comprising administering to an individual in need thereof an effective amount of any composition or formulation described herein.

Actives

In certain embodiments, the compositions and formulations described herein comprise at least two different active agents. In some embodiments, the at least two active agents comprise at least two active agents that are suitable for the treatment of high IOP including glaucoma, ocular hypertension, or a combination thereof. In certain embodiments, the at least two active agents comprise at least two active agents selected from the group consisting of a carbonic anhydrase inhibitor, a prostaglandin, and a beta blocker.

In some embodiments, the compositions and formulations described herein comprise at least two different active agents (i.e., a first active agent and a second active agent). In some instances, the at least two different active agents are both active agents suitable for the treatment of high IOP including glaucoma, ocular hypertension, or a combination thereof. In some embodiments, the first active agent (i.e., one of the at least two different active agents) is a carbonic anhydrase inhibitor. In certain embodiments, the carbonic anhydrase inhibitor is dorzolamide or a pharmaceutically acceptable salt thereof. In specific embodiments, the pharmaceutically acceptable salt of dorzolamide is dorzolamide hydrochloride.

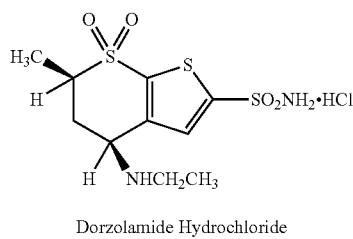

Dorzolamide Hydrochloride

In certain embodiments, the carbonic anhydrase inhibitor (e.g., dorzalamide or dorzolamide hydrogen chloride) is present in a composition or formulation described herein in an amount of about 0.025-5 wt %, or about 1-3 wt %, about 2 wt %, or about 2.2 wt %.

In certain embodiments, the second active agent (i.e., one of the at least two different active agents) is a hypotensive agent (e.g., an ophthalmic hypotensive agent). In some embodiments, the hypotensive agent is a prostaglandin. In some embodiments, the prostaglandin is a $PGF_{2\alpha}$ prostaglandin. In some embodiments, the $PGF_{2\alpha}$ prostaglandin is latanoprost.

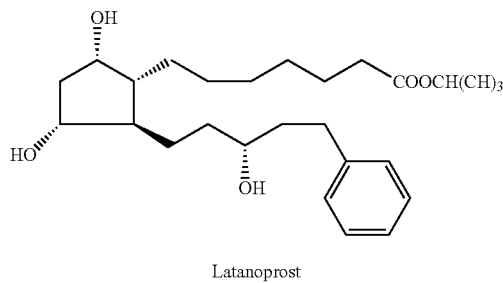

Latanoprost

In some embodiments, the hypotensive agent (e.g., a prostaglandin, such as a $PGF_{2\alpha}$ prostaglandin such as latanoprost) is present in a composition or formulation described herein in an amount of about 0.001-5 wt %, about 0.003-0.01 wt %, or about 0.005 wt %.

In some embodiments, the at least two different active agents for the treatment of glaucoma comprise a beta blocker.

In certain embodiments, a composition or formulation described herein further comprises a third active agent. In some embodiments, the third active agent is a beta blocker. In certain embodiments, the beta blocker is timolol or a pharmaceutically acceptable salt thereof. In some embodiments, the pharmaceutically acceptable salt of timolol is timolol maleate.

In some instances, the at least two different active agents for the treatment of high IOP including glaucoma, ocular hypertension, or a combination thereof comprise a carbonic anhydrase inhibitor and a prostaglandin. In certain embodiments, the at least two different active agents for the treatment of high IOP including glaucoma, ocular hypertension, or a combination thereof comprise dorzolamide or a pharmaceutically acceptable salt thereof as the carbonic anhydrase inhibitor and latanoprost as the prostaglandin. Dorzolamide and latanoprost are useful for the treatment of intraocular hypertension and antiglaucoma topical therapy; the increase in uveoscleral flow and the reduction in the production of aqueous humor are complementary mechanisms reduced respectively by each of these agents.

In some instances, the at least two different active agents for the treatment of high IOP including glaucoma, ocular hypertension, or a combination thereof comprise a carbonic anhydrase inhibitor, a prostaglandin, and a beta blocker. In certain embodiments, the at least two different active agents for the treatment of high IOP including glaucoma, ocular hypertension, or a combination thereof comprise dorzolamide or a pharmaceutically acceptable salt thereof, latanoprost, and timolol.

In certain embodiments, actives described herein are present in a composition or formulation described herein in a therapeutically effective amount. It is to be understood that in some instances, a therapeutically effective amount of an active when combined with a different active is less than a therapeutically effective amount of the active if administered separately or individually.

Stability

In certain embodiments, the formulations disclosed herein provide chemical stability of the at least two active agents. In other words, in certain embodiments, compositions and formulations disclosed herein maintain the stability of the at least two active agents and/or inhibit degradation of the at least two active agents contained therein. In certain instances, chemically stable compositions and formulations provided herein comprise a first active agent that is chemically stable in the composition or formulation and a second active agent that is chemically stable in the composition or formulation. In some instances, chemically stable includes thermal stability. Thus, in some embodiments, compositions, formulations and active agents (e.g., as formulated) described herein are thermally stable. In certain embodiments, compositions, formulations and active agents (e.g., as formulated) described herein are thermally stable at reduced temperature, at room temperature, at ambient temperatures, at about 25° C., at elevated temperatures, at about 40° C., or the like.

In some embodiments, the compositions and formulations disclosed herein are physical stable. In certain embodiments, physical stability includes the maintenance of a suitable physical form of one or both of the at least two active agents within a composition or formulation described herein. In certain embodiments, physically stable ophthalmic and/or topically active formulations comprising a first active agent, a second active agent and a liquid medium (e.g., aqueous medium) described herein, substantially retain their ophthalmic and/or topical activity after storage. In some instances, such compositions substantially retain their ophthalmic and/or topical active after storage as determined by whether or not the first and/or second active agents substantially retain the level of dissolution in a liquid medium as initially formulated or measured. In certain embodiments, physically stable ophthalmic and/or topically active formulations comprising a first active agent, a second active agent and a liquid medium (e.g., aqueous medium) described herein, substantially retain the level of dissolution in a liquid medium as initially formulated or measured. In some instances, determination of the level of physical stability of a composition and/or the level of dissolution of agents within a composition or formulation described herein can be determined by measuring the osmolarity of the composition over a period of time.

Latanoprost has scarce stability due to degradation when formulated in an isotonic solution comprising chloride benzalkonium (as a preservative) and buffered at a pH of 6.8. Such formulations must be packed in plastic containers of 2.5 mL and stored at a temperature of between 2° C. and 8° C. in order to avoid degradation. Latanoprost slowly degrades at temperatures of 4° C. and 25° C. with linear progression, but degrades with polynomial progression of the second order at temperatures of 50° C. and 75° C. Although the rate of degradation at temperatures between 4° C. and 25° C. is not significant, at higher temperatures the rate of degradation increases substantially. For example, at temperatures of 50° C. and 75° C., the time taken by the concentration of latanoprost to drop to 90% of an initial content is 198 and 32 hours, respectively. As a result, prior art latanoprost formulations were refrigerated for storage, and prior art latanoprost formulations were not stored at temperatures above about 20° C. and above (including at temperatures of about 25° C. and above; at temperatures of about 28° C. and above; at temperatures of about 30° C. and above) for extended periods of time.

Provided herein are stable compositions and formulations comprising a prostaglandin (e.g., latanoprost), wherein the prostaglandin (e.g., latanoprost) is stable in the composition (e.g., upon storage). In specific embodiments, the prostaglandin (e.g., latanoprost) is thermally stable in the composition or formulation (e.g., upon storage). In some embodiments, the prostaglandin (e.g., latanoprost) is formulated with a stabilizing agent (e.g., a cyclodextrin, such as hydroxypropyl-β-cyclodextrin). In more specific embodiments, the amount of latanoprost in a composition or formulation described herein after storage at 25° C. for 6 months is about 97% or more, about 98% or more, about 99% or more of an initial amount of latanoprost in the composition or formulation. In certain instances, the initial amount of latanoprost in the composition or formulation refers to the amount of latanoprost in the composition or formulation at any time ($t_0$) that the amount of latanoprost is measured and later compared against (e.g., when the composition or formulation is first prepared or one month after the composition or formulation is first prepared). In some embodiments, the amount of latanoprost in a composition or formulation described herein after storage at 25° C. for 5 months is about 97% or more, about 98% or more, about 99% or more of an initial amount of latanoprost in the composition or formulation. In certain embodiments, the amount of latanoprost in a composition or formulation described herein after storage at 25° C. for 4 months is about 99% or more of an initial amount of latanoprost in the composition or formulation. In some embodiments, the amount of latanoprost in a composition or formulation described herein after storage at 40° C. for 6 months is about 97% or more, about 98% or more, about 99% or more of an initial amount of latanoprost in the composition or formulation. In certain embodiments, the amount of latanoprost in a composition or formulation described herein after storage at 40° C. for 5 months is about 99% or more of an initial amount of latanoprost in the composition or formulation. In specific embodiments, the pH of a formulation having such a stability has a pH between about 5.8 and 6.5, including a pH selected of about 5.8, about 5.9, about 6.0, about 6.1, about 6.2, about 6.3, about 6.4 or about 6.5. In further or alternative embodiments, the composition further comprises a carbonic anhydrase inhibitor (e.g., dorzolamide or dorzolamide hydrogen chloride) and a cyclodextrin (e.g., hydroxypropyl-β-cyclodextrin). In more specific embodiments, the composition or composition comprises a carbonic anhydrase inhibitor (e.g., dorzolamide or dorzolamide hydrogen chloride), a prostaglandin (e.g., a $PGF_{2\alpha}$ prostaglandin such as latanoprost), a stabilizer (e.g., a cyclodextrin, such as hydroxypropyl-β-cyclodextrin), and a liquid medium (e.g., an aqueous medium).

Provided herein are compositions and formulations comprising a carbonic anhydrase inhibitor (e.g., dorzolamide or dorzolamide hydrogen chloride), wherein the carbonic anhydrase inhibitor (e.g., dorzolamide or dorzolamide hydrogen chloride) is stable in the composition (e.g., upon storage). In specific embodiments, the carbonic anhydrase inhibitor (e.g., dorzolamide or dorzolamide hydrogen chloride) is thermally stable in the composition or formulation (e.g., upon storage). In more specific embodiments, the amount of dorzolamide or dorzolamide hydrogen chloride in a composition or formulation described herein after storage at 25° C. for 6 months is about 93% or more, about 94% or more, about 95% or more, about 96% or more, about 97% or more, about 98% or more, about 99% or more of an initial amount of dorzolamide or dorzolamide hydrogen chloride in the composition or formulation. In certain instances, the initial amount of dorzolamide or dorzolamide hydrogen chloride in the composition or formulation refers to the amount of dorzolamide or dorzolamide hydrogen chloride in the composition or formulation at any time ($t_0$) that the amount of dorzolamide or dorzolamide hydrogen chloride is measured and later compared against (e.g., when the composition or formulation is first prepared or one month after the composition or formulation is first prepared). In some embodiments, the amount of dorzolamide or dorzolamide hydrogen chloride in a composition or formulation described herein after storage at 25° C. for 5 months is about 94% or more, about 95% or more, about 96% or more, about 97% or more, about 98% or more, about 99% or more of an initial amount of dorzolamide or dorzolamide hydrogen chloride in the composition or formulation. In certain embodiments, the amount of dorzolamide or dorzolamide hydrogen chloride in a composition or formulation described herein after storage at 25° C. for 4 months is about 95% or more, about 96% or more, about 97% or more, about 98% or more, about 99% or more of an initial amount of dorzolamide or dorzolamide hydrogen chloride in the composition or formulation. In some embodiments, the amount of dorzolamide or dorzolamide hydrogen chloride in a composition or formulation described herein after storage at 25° C. for 3 months is about 97% or more, about 98% or more, about 99% or more of an initial amount of dorzolamide or dorzolamide hydrogen chloride in the composition or formulation. In certain embodiments, the amount of dorzolamide or dorzolamide hydrogen chloride in a composition or formulation described herein after storage at 25° C. for 2 months is about 99% or more of an initial amount of dorzolamide or dorzolamide hydrogen chloride in the composition or formulation. In some embodiments, the amount of dorzolamide or dorzolamide hydrogen chloride in a composition or formulation described herein after storage at 40° C. for 6 months is about 90% or more, about 91% or more, about 92% or more, about 93% or more, about 94% or more, about 95% or more, about 96% or more, about 97% or more, about 98% or more, about 99% or more of an initial amount of dorzolamide or dorzolamide hydrogen chloride in the composition or formulation. In certain embodiments, the amount of dorzolamide or dorzolamide in a composition or formulation described herein after storage at 40° C. for 5 months is about 94% or more, about 95% or more, about 96% or more, about 97% or more, about 98% or more, about 99% or more of an initial amount of dorzolamide or dorzolamide in the composition or formulation. In some embodiments, the amount of dorzolamide or dorzolamide hydrogen chloride in a composition or formulation described herein after storage at 40° C. for 4 months is about 91% or more, about 92% or more, about 93% or more, about 94% or more, about 95% or more, about 96% or more, about 97% or more, about 98% or more, about 99% or more of an initial amount of dorzolamide or dorzolamide hydrogen chloride in the composition or formulation. In certain embodiments, the amount of dorzolamide or dorzolamide in a composition or formulation described herein after storage at 40° C. for 3 months is about 93% or more, about 94% or more, about 95% or more, about 96% or more, about 97% or more, about 98% or more, about 99% or more of an initial amount of dorzolamide or dorzolamide in the composition or formulation. In some embodiments, the amount of dorzolamide or dorzolamide hydrogen chloride in a composition or formulation described herein after storage at 40° C. for 2 months is about 96% or more, about 97% or more, about 98% or more, about 99% or more of an initial amount of dorzolamide or dorzolamide hydrogen chloride in the composition or formulation. In certain embodiments, the amount of dorzolamide or dorzolamide in a composition or formulation described herein after storage at 40° C. for 1 months is about 99% or more of an initial amount of dorzolamide or dorzolamide in the composition or formulation. In specific embodiments, the pH of a formulation having such a stability has a pH between about 5.8 and 6.5, including a pH selected of about 5.8, about 5.9, about 6.0, about 6.1, about 6.2, about 6.3, about 6.4 or about 6.5. In further or alternative embodiments, the composition further comprises a prostaglandin (e.g., a PGF$_{2\alpha}$ prostaglandin such as latanoprost) and a cyclodextrin (e.g., hydroxypropyl-β-cyclodextrin). In more specific embodiments, the composition or composition comprises a carbonic anhydrase inhibitor (e.g., dorzolamide or dorzolamide hydrogen chloride), a prostaglandin (e.g., a PGF$_{2\alpha}$ prostaglandin such as latanoprost), a stabilizer (e.g., a cyclodextrin, such as hydroxypropyl-β-cyclodextrin), and a liquid medium (e.g., an aqueous medium).

Provided herein are compositions and formulations comprising a carbonic anhydrase inhibitor (e.g., dorzolamide or dorzolamide hydrogen chloride), a prostaglandin (e.g., a PGF$_{2\alpha}$ prostaglandin such as latanoprost), a stabilizer (e.g., a cyclodextrin, such as hydroxypropyl-β-cyclodextrin), and a liquid medium (e.g., an aqueous medium). In certain embodiments, such compositions and formulations are physically stable. In some instances, physical stability is determined as an ability of composition or formulation to maintain a certain osmolarity. In some embodiments, physically stable compositions and formulations described herein substantially maintain an osmolarity (e.g., a variation of less than about 2% over a period of about 5 months at 25° C.). In certain embodiments, physically stable compositions and formulations described herein comprise and substantially maintain an osmolarity and/or pH that is physiologically acceptable. In specific instances, a physiologically acceptable osmolarity is about 280 mOsm/L to about 320 mOsm/L. In some embodiments, compositions and formulations described herein are substantially stable (physical and/or chemical) under physiologically acceptable osmolarities and/or physiologically acceptable pH values.

In some embodiments, formulations disclosed herein provide suitable stability to a prostaglandin (e.g., a PGF$_{2\alpha}$ prostaglandin such as latanoprost). In certain embodiments, the stability of latanoprost is maintained in the presence of a stabilizer (e.g., a cyclodextrin, such as hydroxypropyl-β-cyclodextrin) at a pH lower than 6.7-6.8. Surprisingly, in some embodiments, the stability of a prostaglandin (e.g., a PGF$_{2\alpha}$ prostaglandin such as latanoprost) in the presence of a stabilizer (e.g., a cyclodextrin, such as hydroxypropyl-β-cyclodextrin) and a carbonic anhydrase inhibitor (e.g., dorzolamide or dorzolamide hydrogen chloride) is maintained at a pH between about 5.8 and 6.5, including a pH selected of about 5.8, about 5.9, about 6.0, about 6.1, about 6.2, about 6.3, about 6.4 or about 6.5. Thus, in specific embodiments, compositions and formulations described herein have a pH of about 5.8 to about 6.5. Thus, in specific embodiments, compositions and formulations described herein have a pH of about 5.8 to about 6.4. Thus, in specific embodiments, compositions and formulations described herein have a pH of about 5.8 to about 6.3. Thus, in specific embodiments, compositions and formulations described herein have a pH between about 5.8 and 6.5, including a pH selected of about 5.8, about 5.9, about 6.0, about 6.1, about 6.2, about 6.3, about 6.4 or about 6.5.

Provided herein are compositions and formulations comprising a carbonic anhydrase inhibitor (e.g., dorzolamide or dorzolamide hydrogen chloride), a prostaglandin (e.g., a PGF$_{2\alpha}$ prostaglandin such as latanoprost), a stabilizer (e.g., a cyclodextrin, such as hydroxypropyl-β-cyclodextrin), and a liquid medium (e.g., an aqueous medium), wherein the composition or formulation has a pH between about 5.8 and 6.5, including a pH selected of about 5.8, about 5.9, about 6.0, about 6.1, about 6.2, about 6.3, about 6.4 or about 6.5.

Tolerability

In further or alternative embodiments, formulations disclosed herein comprise a pH that is well-tolerated by the eye. In some embodiments, a pH that is well-tolerated by the eye does not cause symptoms of eye irritation when the formulations are administered to the eye. In certain embodiments, symptoms of eye irritation include conjunctival burning and/or redness of the ocular surface. In some embodiments, by having a pH that is well-tolerated by the eye, formulations disclosed herein improve patient compliance with a treatment regimen comprising administration of at least two different active agents for the treatment of high IOP including glaucoma, ocular hypertension, or a combination thereof.

Pharmaceutical compositions comprising dorzolamide hydrochloride (e.g., 2.2% by weight, 2% by weight of the free base) have a maximum solubility at a pH of 5.6 (about 50 mg/mL). Because of structural characteristics of dorzolamide hydrochloride, it is not very soluble at neutral pH levels. Indeed, the solubility of dorzolamide hydrochloride decreases significantly at pH values in excess of 5.6 and, absent the use of other solubilizing techniques, ophthalmic compositions comprising dorzolamide hydrochloride are not typically used at a pH of greater than 5.65. Such compositions are poorly tolerated by the eye, however, causing burning and/or redness of the ocular surface and having reduced levels of patient compliance. Furthermore, formulations of dorzolamide hydrochloride are often dosed multiple times a day (e.g., 3 times per day), and the stinging/burning of the formulation becomes quite noticeable and unpleasant to the patient.

In certain instances, pH values that are well-tolerated by the eye are greater than 5.65. In some instances, pH values that are well-tolerated by the eye have decreased incidences of burning and/or redness of the ocular surface compared the burning and/or redness of the ocular surface caused by administration of a composition or formulation having a pH of 5.65 or less. In some instances, pH values that are well-tolerated by the eye are pH values that do not cause burning and/or redness of the ocular surface when administered to the eye. In certain instances, compositions and formulations with pH values that are well-tolerated by the eye have increased levels of patient compliance (and thereby increased efficacy) compared to less-tolerated compositions (e.g., compositions with pH values of 5.65 or less).

A series of experiments, discussed further below, unexpectedly indicate that dorzolamide or a pharmaceutically acceptable salt thereof can be formulated with latanoprost at a pH that is not considered appropriate for solubilizing dorzolamide (e.g., above 5.65) or for the formulation of latanoprost (e.g., 6.7-6.8). Furthermore, the pH range that provides appropriate solubility and stability of dorzolamide and latanoprost is also well-tolerated by the eye when used in topical treatment of high IOP including glaucoma, ocular hypertension, or a combination thereof. By virtue of being well-tolerated by the eye, the formulations disclosed herein further improve patient compliance with a treatment regimen comprising both of the actives. This is particularly true with respect to dorzolamide, which is administered at pH levels below 5.65, causing a series of side effects including conjunctival burning and redness of the ocular surface.

Stabilizers

In some embodiments, compositions and formulations described herein comprise a stabilizing agent. In certain embodiments, the stabilizing agent enhances the chemical stability, physiological, and/or physical stability of the composition or formulation. In specific embodiments, stabilizing agents useful herein include, by way of non-limiting example, one or more cyclodextrin (e.g., hydroxypropyl-β-cyclodextrin).

In some embodiments, the formulations disclosed herein comprise a cyclodextrin. In certain embodiments, the cyclodextrin is HP-β-cyclodextrin. Other possible stabilizing agents include, by way of non-limiting example, lipid emulsions of polyvinilic alcohol.

In certain embodiments, the amount of stabilizer (e.g., a cyclodextrin, such as hydroxypropyl-β-cyclodextrin) present is about 1% or more to about 8% or more, going respectively from a pH of 6.0 to a pH of 6.8 (e.g., when the hydroxypropyl-β-cyclodextrin is characterized by an average degree of substitution of 6.1 (determined by NMR) and an average molecular weight of 1630 g/mol). Other hydroxypropyl-β-cyclodextrins (e.g., characterized by a different degree of substitution) are also suitably used in the formulations described herein, and in certain embodiments, are utilized by adjusting the concentration of the cyclodextrin to obtain similar results.

In some embodiments, a composition or formulation described herein comprises about 2 wt % to about 10 wt % of a stabilizer (e.g., a cyclodextrin such as HP-β-cyclodextrin).

Formulations

In certain embodiments, compositions and formulations described herein comprise a carbonic anhydrase inhibitor (e.g., dorzolamide or a pharmaceutically acceptable salt thereof, such as dorzolamide hydrochloride), a hypotensive agent (e.g., an a $PGF_{2\alpha}$ prostaglandin such as latanoprost), and a stabilizer (e.g., a cyclodextrin, such as hydroxypropyl-β-cyclodextrin). In some embodiments, the carbonic anhydrase inhibitor (e.g., dorzolamide or a pharmaceutically acceptable salt thereof, such as dorzolamide hydrochloride) and a hypotensive agent (e.g., an a $PGF_{2\alpha}$ prostaglandin such as latanoprost) are present in a therapeutically acceptable amount.

In certain embodiments, formulations (e.g., aqueous formulations) prepared according to the instant disclosure comprise components in the weight percentages set forth below (Table 1), and have a pH between about 5.8 and 6.5, including a pH selected of about 5.8, about 5.9, about 6.0, about 6.1, about 6.2, about 6.3, about 6.4 or about 6.5.

TABLE 1

| Component | Amount |
| --- | --- |
| Dorzolamide hydrochloride | 0.025-5.0% |
| Latanoprost | 0.001-5.0% |
| HP-β-cyclodextrin | 0.010-50.0% |

According to certain specific embodiments, compositions disclosed herein comprise the components in the weight proportions set forth in Table 2, and have a pH between about 5.8 and 6.5, including a pH selected of about 5.8, about 5.9, about 6.0, about 6.1, about 6.2, about 6.3, about 6.4 or about 6.5.

TABLE 2

| Component | Amount |
| --- | --- |
| Dorzolamide hydrochloride | 1.0-3.0% |
| Latanoprost | 0.003-0.010% |
| HP-β-cyclodextrin | 2.00-10.0% |

Formulations disclosed herein optionally further comprise additional anti-glaucoma agents. In some embodiments, an additional anti-glaucoma agent is a beta blocker. In certain embodiments, the beta blocker is timolol or a pharmaceutically acceptable salt thereof. In certain specific embodiments, timolol is present as its maleate salt at 0.1% by weight.

Formulations disclosed herein optionally further comprise hyaluronic acid or a pharmaceutically acceptable salt thereof, e.g., sodium hyaluronate. In addition to its recognized functions, including as a mucoadhesive agent, the presence of hyaluronate in the composition increases the ocular bioavailability of dorzolamide. In some embodiments, sodium hyaluronate is present in the formulations at 0.01-0.10 wt %. In certain specific embodiments, sodium hyaluronate is present in the formulations at about 0.05 wt %.

Formulations disclosed herein also optionally further comprise one or more ophthalmic excipient. Ophthalmic excipients include, by way of non-limiting example, at least one agent selected from a mucoadhesive, a preservative, a pH-adjusting agent, a tonicity-adjusting agent, a buffering agent, an antioxidant, a chelating agent, an antimicrobial preservative, a chemical preservative, or a combination thereof. In some embodiments, the mucoadhesive is hyaluronic acid or a pharmaceutically acceptable salt thereof (e.g., sodium hyaluronate), polyvinyl alcohol, polyvinyl-pyrrolidone, hydroxypropyl-methylcellulose, carboxymethyl-cellulose, hydroxyethyl cellulose, a poloxamer, alginic acid, chitosan, xanthan gum, carrageenan, acrylic acid, acrylic acid derivatives, or a combination thereof. In some embodiments, mucoadhesives are present in the formulation at 0.01-10 wt %. In some embodiments, the preservative is benzalkonium chloride, chlorobutanol, phenylmercuric acetate, phenylmercuric nitrate, polyhexanide, cetrimide, cetylpyridinium chloride, EDTA, or a combination thereof. In some embodiments, the pH-adjusting agent is hydrochloric acid, boric acid, acetic acid, sodium hydroxide, potassium hydroxide, or a combination thereof. In some embodiments, the tonicity-adjusting agent is sodium chloride, potassium chloride, mannitol, glycerol, sorbitol, xylitol, or a combination thereof. In some embodiments, the buffering agent is an acetate buffer, a citrate buffer, a phosphate buffer, a borate buffer, or a combination thereof. In some embodiments, the antioxidant is sodium metabisulfite, sodium thiosulfate, acetyl cysteine, BHA, BHT, vitamin E, ascorbic acid, 6-hydroxy-2,5,7,8-tetramethylchroman-2-carboxylic acid (TROLOX®), or a combination thereof. In specific embodiments, compositions described herein comprise EDTA in an amount of about 0.03 wt %. In some embodiments, a composition or formulation described herein comprises a tonicity adjusting agent (e.g., sodium chloride) in an amount of about 0.13 wt % (or is prepared using such an amount of tonicity adjusting agent). In certain embodiments, preservatives are present in an amount of about 0.003 wt %.

In some embodiments, a composition or formulation disclosed herein does not contain a buffer system. In further embodiments, a composition or formulation disclosed herein does not contain an antioxidant. In some embodiments, a composition disclosed herein contains neither a buffer system nor an antioxidant. In some embodiments, a composition or formulation disclosed herein does not contain a antimicrobial preservative.

Also disclosed herein is a method of treating high IOP including glaucoma, ocular hypertension, or a combination thereof comprising topically administering the formulations disclosed herein to the eye of a patient in need thereof. Dosing and the frequency of administration depend on the severity of the condition and individual characteristics of the patient. A typical frequency of administration for the treatment of high IOP including glaucoma, ocular hypertension, or a combination thereof is daily, e.g., once daily, twice daily, thrice daily, etc. The formulations disclosed herein are mixed with suitable carriers, excipients, diluents, or a combination thereof to generate a preparation for topical administration to the eye. Examples of suitable preparations include eye drops, ophthalmic gels and ointments, and collyria.

In specific embodiments, compositions or formulations set forth herein are prepared by combining the components set forth in Table 3. In more specific embodiments, the composition or formulation is formulated in an aqueous medium (e.g., water), e.g., as a solution. In still more specific embodiments, the composition or formulation as an osmolarity of about 280 mOsm/L to about 320 mOsm/L.

TABLE 3

| Ingredient | Weight Percentage |
| --- | --- |
| Dorzolamide•hydrochloride | 2.23% |
| Latanoprost | 0.005% |
| HP-β-Cyclodextrin | 2.0%-10% |
| NaCl | 0.135% |
| Polyhexanide (PHMB) | 0.003% |
| Disodium EDTA | 0.036% |
| NaOH (4N) | q.b. pH = 6.10 |
| Sodium hyaluronate (HTL) | 0.05% |

EXAMPLES

Example 1

A Representative Ophthalmic Latanoprost-Dorzolamide Formulation at pH 6.1

In certain instances, an ophthalmic collyrium is prepared by combining the agents set forth in Table 4:

TABLE 4

| Ingredient | Weight Percentage |
| --- | --- |
| Dorzolamide•hydrochloride | 2.23% |
| Latanoprost | 0.005% |
| HP-β-Cyclodextrin | 2.0%-10% |
| NaCl | 0.135% |
| Polyhexanide (PHMB) | 0.003% |
| Disodium EDTA | 0.036% |
| NaOH (4N) | q.b. pH = 6.10 |
| Sodium hyaluronate (HTL) | 0.05% | pH = 6.10 Osmolarity = 280-320 mOsm/L

Example 2

Stability Analysis of Ophthalmic Latanoprost-Dorzolamide Formulations

The formulation of Example 1 is stored for six months at two different temperatures (25 and 40° C.), and the percentage of active ingredients remaining in the formulation is assessed each month following the initiation of storage. The results of the stability analysis for the formulation of Example 1 are summarized in Tables 5-6.

TABLE 5

| Storage Temperature | Months of | pH | Osmolarity | Latanoprost Remaining (%) | Dorzolamide Remaining (%) |
| --- | --- | --- | --- | --- | --- |
| 25° C. | | 6.0-6.2 | 250-320 mOsm/Kg | 90.0%-110% | 90.0%-110% |
| | 1 | 6.10 | 305 | 98.5 | 101.1 |
| | 2 | 6.10 | 307 | 100.2 | 100.5 |
| | 3 | 6.08 | 307 | 99.8 | 99.5 |
| | 4 | 6.09 | 311 | 99.5 | 100.1 |
| | 5 | 6.11 | 310 | 97.6 | 99.8 |
| | 6 | 6.11 | 311 | 98.4 | 101.0 |

TABLE 6

| Storage Temperature | Months of | pH | Osmolarity | Latanoprost Remaining (%) | Dorzolamide Remaining (%) |
| --- | --- | --- | --- | --- | --- |
| 40° C. | | 6.0-6.2 | 250-320 mOsm/Kg | 90.0%-110% | 90.0%-110% |
| | 1 | 6.10 | | 99.8 | 100.1 |
| | 2 | 6.11 | | 101.2 | 99.9 |
| | 3 | 6.10 | | 99.8 | 99.5 |
| | 4 | 6.13 | | 98.7 | 100.5 |
| | 5 | 6.12 | | 99.5 | 99.6 |
| | 6 | 6.13 | | 98.5 | 98.9 |

A formulation similar to the exemplified product in Example 1, but with a pH equal to 6.8, is prepared for comparison in a stability analysis. The composition of the formulation is described in the Table 7.

TABLE 7

| Ingredient | Weight Percentage |
| --- | --- |
| Dorzolamide•hydrochloride | 2.23% |
| Latanoprost | 0.005% |
| HP-β-Cyclodextrin | 8.0% |
| NaCl | 0.135% |
| Polyhexanide (PHMB) | 0.003% |
| Disodium EDTA | 0.036% |
| NaOH (4N) | q.b. pH = 6.80 |
| Sodium hyaluronate (HTL) | 0.05% | pH = 6.80 Osmolarity = 310 mOsm/L

The formulation at pH=6.8 was stored for six months at two different temperatures (25 and 40° C.), and the percentage of active ingredients remaining in the formulation was assessed at each month following the initiation of storage.

The results of the stability analysis are summarized Tables 8 and 9.

TABLE 8

| Storage Temperature | Months of | pH | Osmolarity | Latanoprost Remaining (%) | Dorzolamide Remaining (%) |
|---|---|---|---|---|---|
| 25° C. |  | 6.7-6.9 | 250-320 mOsm/kg | 90.0%-110% | 90.0%-110% |
|  | 1 | 6.80 | 313 | 101.3 | 101 |
|  | 2 | 6.77 | 306 | 102.5 | 99.1 |
|  | 3 | 6.75 | 309 | 104.1 | 100.4 |
|  | 4 | 6.85 | 310 | 102.9 | 98.5 |
|  | 5 | 6.82 | 306 | 102.6 | 94.3 |
|  | 6 | 6.83 | 302 | 99.8 | 92.9 |

TABLE 9

| Storage Temperature | Months of | pH | Osmolarity | Latanoprost Remaining (%) | Dorzolamide Remaining (%) |
|---|---|---|---|---|---|
| 40° C. |  | 5.7-6.9 | 250-320 mOsm/kg | 90.0%-110% | 90.0%-110% |
|  | 1 | 6.75 | 313 | 102.1 | 98.8 |
|  | 2 | 6.80 | 307 | 101.3 | 96.0 |
|  | 3 | 6.82 | 311 | 105.3 | 92.7 |
|  | 4 | 6.87 | 307 | 100.1 | 90.9 |
|  | 5 | 6.95 | 305 | 102.6 | 93.6 |
|  | 6 | 6.89 | 303 | 97.4 | 89.5 |

As can be seen in the tables above, a formulation comprising latanoprost, dorzolamide, HP-β-cyclodextrin, and sodium hyaluronate with a pH of 6.1 is stable under long-term storage at room and elevated temperatures. Conversely, a similarly formulated composition with a pH of 6.8 yields significant decomposition of the active agents under identical storage conditions. Thus, formulating latanoprost and dorzolamide as described herein results in an ophthalmic composition that achieves superior long-term stability of the active agents, and is suitable for coadministration of the drugs for the treatment of high IOP including glaucoma, ocular hypertension, or a combination thereof.

Example 3

Stability of Dorzolamide at 25° C. in a Formulation According to Example 1 with HP-β-cyclodextrin at 8.0% and Varying pH Levels Multiple formulations are prepared according to Example 1, with the concentration of HP-β-cyclodextrin at 8.0%, and the pH varying between 6.1 and 6.8. The formulations re stored at 25° C. for up to six months, and the percentage of dorzolamide remaining in the formulation is measured each month following initiation of storage. The results are summarized in Tables 10-13.

As is seen in Tables 10-13, formulations having a pH above 6.20 exhibit degradation in dorzolamide that is excessive or at the limit of acceptability for the preservation of the dorzolamide-latanoprost combination at ambient temperature. Formulations prepared with a pH below 6.20 achieve suitable stability of dorzolamide for long-term storage and subsequent coadministration of the active agents.

TABLE 10

|  |  | pH | Titration % Dorzolamide |
|---|---|---|---|
| Dorzolamide 25° C. pH = 6.1 | Months | 6.0-6.2 | 90.0-110% |
|  | 1 | 6.10 | 101 |
|  | 2 | 6.10 | 99.8 |
|  | 3 | 6.08 | 100 |
|  | 4 | 6.09 | 100 |
|  | 5 | 6.11 | 98.8 |
|  | 6 | 6.11 | 99.9 |

TABLE 11

|  |  | pH | Titration % Dorzolamide |
|---|---|---|---|
| Dorzolamide 25° C. pH = 6.2 | Months | 6.1-6.3 | 90.0-110% |
|  | 1 | 6.20 | 101 |
|  | 2 | 6.21 | 99.8 |
|  | 3 | 6.18 | 99.5 |
|  | 4 | 6.21 | 97.5 |
|  | 5 | 6.23 | 97.0 |
|  | 6 | 6.23 | 97.8 |

TABLE 12

|  |  | pH | Titration % dorzolamide |
|---|---|---|---|
| Dorzolamide 25° C. pH = 6.5 | Months | 6.4-6.6 | 90.0-110% |
|  | 1 | 6.52 | 102 |
|  | 2 | 6.52 | 99.8 |
|  | 3 | 6.60 | 97.5 |
|  | 4 | 6.55 | 95.5 |
|  | 5 | 6.60 | 93.8 |

TABLE 13

|  |  | pH | Titration % dorzolamide |
|---|---|---|---|
| Dorzolamide 25° C. pH = 6.8 | Months | 6.7-6.9 | 90.0-110% |
|  | 1 | 6.80 | 101 |
|  | 2 | 6.77 | 99.1 |
|  | 3 | 6.75 | 100 |
|  | 4 | 6.85 | 98.5 |
|  | 5 | 6.82 | 94.3 |

Example 4

Stability of Dorzolamide Formulations According to Example 1 at 40° C. with HP-β-cyclodextrin at 8.0% and Varying pH The stability of formulations according to Example 1 with HP-β-cyclodextrin at 8.0% and with varying pH levels are also assessed under elevated temperatures (40° C.), as set forth in Table 14. The remaining percentage of dorzolamide in the formulations was measured at 10, 15, and 30 days following initiation of storage. As with the stability studies at ambient temperature, a pH above 6.2 resulted in significant decomposition of dorzolamide under the accelerated conditions. Formulations prepared according to the disclosure herein, however, maintained suitable concentrations of dorzolamide even under the harsher conditions.

TABLE 14

|  | 10 days | 15 days | 30 days |
|---|---|---|---|
| Titration % dorzolamide pH = 6.10 (a) | 101% | 99.5% | 101% |
| pH(a) | 6.10 | 6.12 | 6.12 |
| Osmolarity (a) | 289 | 285 | 290 |
| Titration % dorzolamide pH = 6.20 (b) | 100% | 98.1% | 97.2% |
| pH(b) | 6.21 | 6.23 | 6.23 |
| Osmolarity (b) | 304 | 307 | 309 |
| Titration % dorzolamide pH = 6.50 (c) | 99% | 95.6% | 89.6% |
| pH(c) | 6.46 | 6.49 | 6.50 |
| Osmolarity (c) | 283 | 287 | 283 |
| Titration % dorzolamide pH = 6.80 (d) | 100% | 92.6% | 86.6% |
| pH(d) | 6.78 | 6.70 | 6.70 |
| Osmolarity (d) | 311 | 305 | 309 |

Example 5

Acute Ocular Tolerability of an Ophthalmic Latanoprost-Dorzolamide Formulation at pH=6.1 Compared to an Equivalent Formulation at pH=6.8 and a Placebo at pH=6.8

Two drops of each of the formulations described above are instilled in the right eye of each animal 3 times on the same day at an interval of 2 hours. Every group of rabbits consisted of 8 animals (4 males and 4 females).

The condition of the ocular tissue is observed according to the Draize Test. The examination is conducted after the third instillation on the day of the treatment and also 24, 48 and 72 hours after the first instillation, assigning arbitrary scores to the various aspects of the conjunctiva of the iris and cornea. No significant reddening of the conjunctiva is observed for the entire period of the test, both in the eyes treated with the pH=6.1 formulation and in those treated with pH=6.8 formulation, as well as with the placebo. No edema or opacity is observed at the corneal level. In addition, no involvement of the iris is observed. The presence of drainage material stayed at normal level. Mild de-epithelization is observed in three eyes treated with the pH=6.1 formulation and in two eyes treated with the pH=6.8 formulation.

The results obtained show that the ophthalmic solution at pH=6.1 is well tolerated after repeated instillations (three in 6 hours), and there are no difference versus the pH=6.8 formulation and its placebo, also at pH=6.8.

Example 6

Test of an Ophthalmic Latanoprost-Dorzolamide Formulation in an Animal Model of Glaucoma Elevated intraocular pressure is induced in rats by cauterization of three of the four episcleral veins. Following stabilization of intraocular pressure, rats with sustained elevated intraocular pressure levels (typically 1.5-1.8 times normal) are selected for the test. Rats with high intraocular pressure are daily administered either an ophthalmic latanoprost-dorzolamide formulation disclosed herein or the carrier for the formulation alone as a control. In order to assess the efficacy of administering a stable, ophthalmic latanoprost-dorzolamide formulation disclosed herein for the treatment of ocular hypertension and glaucoma, the absolute and relative (percentage from baseline) reduction of intraocular pressure is measured for both groups over a three-month period, and the average values for the test group at various time points are compared to the average values for the control group at the corresponding time points. At the end of the test period, the rats are sacrificed and the extent of retinal ganglion cell death is measured. The extent of ganglion cell death is compared in the test and control groups to assess the efficacy of the formulations disclosed herein in inhibiting the progression or onset of glaucoma induced by ocular hypertension.

Example 7

Clinical Trial of an Ophthalmic Latanoprost-Dorzolamide Formulation for the Treatment of Ocular Hypertension and Primary Open Angle Glaucoma Patients selected for inclusion in the trial have an intraocular pressure greater than 20 mmHg resulting from ocular hypertension or primary open angle glaucoma. Patients included in the trial are also naive (have never been treated for ocular hypertension) and require treatment initiation. Primary outcomes of the study are the absolute value and relative magnitude (percentage from baseline) of intraocular pressure reduction after three months of treatment. The reduction of intraocular pressure is also assessed at one and two months following treatment initiation.

Patients in the test group are topically administered a latanoprost-dorzolamide formulation according to Example 1. Patients in the control group are topically administered either an ophthalmic latanoprost formulation (0.005% latanoprost, XALATAN®) or dorzolamide formulation (2% dorzolamide, TRUSOPT®) daily for three months following recommended dosing procedures. Intraocular pressure is measured by standard tonometry tests (applanation, electronic indentation, or noncontact tonometry).

The absolute and relative reduction of intraocular pressure following administration of a combination latanoprost-dorzolamide formulation disclosed herein is compared to the absolute and relative reduction from administration of each of the individual therapies alone. The average absolute and relative reduction in intraocular pressure following administration of a combination formulation is also compared to the combination of the average results from the single agent therapies to assess the synergy of coadministering the active agents in a single, stable ophthalmic formulation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A stable ophthalmic pharmaceutical composition for the treatment of glaucoma, ocular hypertension, or a combination thereof, the stable ophthalmic pharmaceutical composition comprising: (a) a therapeutically-effective amount of dorzolamide, or a pharmaceutically acceptable salt thereof, (b) a therapeutically-effective amount of latanoprost, and (c) a cyclodextrin, wherein the composition has a pH between about 6.0 and about 6.2, and wherein the composition is stable with respect to degradation of the dorzolamide and latanoprost for at least 4 months.

2. The stable ophthalmic pharmaceutical composition according to claim 1, further comprising a mucoadhesive, a preservative, a pH-adjusting agent, a tonicity-adjusting agent, a buffering agent, an antioxidant, or a combination thereof.

3. The stable ophthalmic pharmaceutical composition according to claim 2, further comprising a therapeutically effective amount of an additional anti-glaucoma agent.

4. The stable ophthalmic pharmaceutical composition according to claim 3, wherein the additional anti-glaucoma agent is a beta blocker.

5. The stable ophthalmic pharmaceutical composition according to claim 4, wherein the beta blocker is timolol.

6. The stable ophthalmic pharmaceutical composition according to claim 1, wherein the pharmaceutically acceptable salt of dorzolamide is dorzolamide hydrochloride.

7. The stable ophthalmic pharmaceutical composition according to claim 1, wherein the cyclodextrin is hydroxypropyl-β-cyclodextrin.

8. The stable ophthalmic pharmaceutical composition according to claim 2, wherein the mucoadhesive is hyaluronic acid or a pharmaceutically acceptable salt thereof, polyvinyl alcohol, polyvinyl-pyrrolidone, hydroxypropyl-methylcellulose, carboxymethyl-cellulose, hydroxyethyl cellulose, a poloxamer, alginic acid, chitosan, xanthan gum, carrageenan, acrylic acid, acrylic acid derivatives, or a combination thereof.

9. The stable ophthalmic pharmaceutical composition according to claim 2, wherein the preservative is benzalkonium chloride, chlorobutanol, phenylmercuric acetate, phenylmercuric nitrate, polyhexinide, cetrimide, cetylpyridinium chloride, EDTA, or a combination thereof.

10. The stable ophthalmic pharmaceutical composition of claim 2, wherein the pH-adjusting agent is hydrochloric acid, boric acid, acetic acid, sodium hydroxide, potassium hydroxide, or a combination thereof.

11. The stable ophthalmic pharmaceutical composition of claim 2, wherein the tonicity-adjusting agent is sodium chloride, potassium chloride, mannitol, glycerol, sorbitol, xylitol, or a combination thereof.

12. The stable ophthalmic pharmaceutical composition of claim 2, wherein the buffering agent is an acetate buffer, a citrate buffer, a phosphate buffer, a borate buffer, or a combination thereof.

13. The stable ophthalmic pharmaceutical composition of claim 2, wherein the antioxidant is sodium metabisulfite, sodium thiosulfate, acetyl cysteine, BHA, BHT, vitamin E, ascorbic acid, 6-hydroxy-2,5,7,8-tetramethylchroman-2-carboxylic acid, or a combination thereof.

14. The stable ophthalmic pharmaceutical composition according to claim 1, wherein the composition comprises the following components in the following weight percentages:

| | |
|---|---|
| dorzolamide hydrochloride | 1-3% |
| latanoprost | 0.003-0.01% |
| HP-β-cyclodextrin | 2-10%. |

15. A stable ophthalmic pharmaceutical composition comprising: (a) a therapeutically-effective amount of dorzolamide, or a pharmaceutically acceptable salt thereof, (b) a therapeutically-effective amount of lantanoprost, and (c) a cyclodextrin, wherein the composition has a pH between about 6.0 and about 6.2, and wherein the composition is stable with respect to degradation of the dorzolamide and latanoprost for at least 4 months.

16. The stable ophthalmic pharmaceutical composition according to claim 15, wherein after 6 months of storage at 25° C. or at 40° C., the composition comprises at least 97% of the initial amount of dorzolamide, and at least 98% of the initial amount of latanoprost.

17. A method of treating glaucoma, ocular hypertension, or a combination thereof, comprising topically administering a stable ophthalmic pharmaceutical composition according to claim 1 to the eye of a patient in need thereof.

* * * * *